US011872300B2

(12) United States Patent
Foley et al.

(10) Patent No.: US 11,872,300 B2
(45) Date of Patent: Jan. 16, 2024

(54) COSMETIC COMPOSITIONS COMPRISING POLYETHER POLYMERS

(71) Applicant: P2 SCIENCE, INC., Woodbridge, CT (US)

(72) Inventors: Patrick Foley, New Haven, CT (US); Ashoke Bhattacharjee, Cheshire, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 63 days.

(21) Appl. No.: 17/185,619

(22) Filed: Feb. 25, 2021

(65) Prior Publication Data

US 2021/0275430 A1  Sep. 9, 2021

Related U.S. Application Data

(60) Provisional application No. 63/125,859, filed on Dec. 15, 2020, provisional application No. 63/092,412, filed on Oct. 15, 2020, provisional application No. 63/043,255, filed on Jun. 24, 2020, provisional application No. 62/985,400, filed on Mar. 5, 2020.

(51) Int. Cl.
| | | |
|---|---|---|
| C08G 65/00 | (2006.01) | |
| C08G 65/34 | (2006.01) | |
| A61K 8/86 | (2006.01) | |
| A61K 8/89 | (2006.01) | |
| A61Q 5/02 | (2006.01) | |
| A61Q 5/12 | (2006.01) | |
| A61Q 19/00 | (2006.01) | |
| A61Q 19/10 | (2006.01) | |

(52) U.S. Cl.
CPC ............ *A61K 8/86* (2013.01); *A61K 8/89* (2013.01); *A61Q 5/02* (2013.01); *A61Q 5/12* (2013.01); *A61Q 19/007* (2013.01); *A61Q 19/10* (2013.01); *A61K 2800/10* (2013.01); *A61K 2800/43* (2013.01); *A61K 2800/48* (2013.01); *A61K 2800/522* (2013.01); *A61K 2800/524* (2013.01); *A61K 2800/594* (2013.01)

(58) Field of Classification Search
None
See application file for complete search history.

(56) References Cited

U.S. PATENT DOCUMENTS

| | | |
|---|---|---|
| 2,020,298 A | 11/1935 | Carothers et al. |
| 3,829,505 A | 8/1974 | Johnston |
| 3,980,697 A | 9/1976 | El-Chahawi et al. |
| 4,021,507 A | 5/1977 | Ford |
| 4,070,386 A | 1/1978 | Rossmy |
| 4,218,379 A | 8/1980 | Harris et al. |
| 4,366,270 A | 12/1982 | Ruter |
| 4,381,416 A | 4/1983 | Kyo et al. |
| 5,030,768 A | 7/1991 | Chen et al. |
| 5,264,547 A | 11/1993 | Yamaguchi et al. |
| 5,292,845 A | 3/1994 | Kawasaki et al. |
| 5,531,910 A | 7/1996 | Severns et al. |
| 5,545,601 A | 8/1996 | Le-Khac |
| 5,616,679 A | 4/1997 | Fies et al. |
| 6,355,845 B1 | 3/2002 | Clement et al. |
| 6,359,101 B1 | 3/2002 | O'Connor et al. |
| 6,369,025 B1 | 4/2002 | Trinh et al. |
| 7,355,066 B1 | 4/2008 | Johnson et al. |
| 9,068,091 B2 | 6/2015 | Hofstra et al. |
| 9,982,073 B2 | 5/2018 | Ghandi et al. |
| 10,059,801 B2 * | 8/2018 | Foley .................. C07C 41/01 |
| 10,844,169 B2 * | 11/2020 | Foley .................. C08G 65/34 |
| 11,008,271 B2 | 5/2021 | Yang et al. |
| 11,518,850 B2 * | 12/2022 | Foley .................. C08G 65/34 |
| 2004/0152830 A1 | 8/2004 | Kim et al. |
| 2006/0018977 A1 | 1/2006 | Bruza et al. |
| 2013/0202543 A1 | 8/2013 | Kuper et al. |
| 2017/0057940 A1 | 3/2017 | Foley et al. |
| 2017/0088536 A1 | 3/2017 | Foley et al. |
| 2017/0283553 A1 | 10/2017 | Foley et al. |
| 2021/0230364 A1 | 7/2021 | Bhattacharjee et al. |

FOREIGN PATENT DOCUMENTS

| | | |
|---|---|---|
| DE | 10 2005 025 739 A1 | 12/2006 |
| EP | 0841333 A1 | 5/1998 |
| GB | 1266091 | 3/1972 |
| JP | 2006 273796 A | 10/2006 |
| JP | 2008 050415 A | 3/2008 |
| JP | 4074908 B2 | 4/2008 |
| WO | WO 2006/057086 | 6/2006 |
| WO | WO 2019/029808 A1 | 2/2019 |

(Continued)

OTHER PUBLICATIONS

Bai, et al., "Strategies and Methods for the Synthesis of Anticancer Natural Product Neopeltolide and its Analogs," *Curr Org Chem.*, vol. 19, No. 10, 33 pages, (2015); DOI: 10.2174/1385272819666150119225149.

Cahn et al, "Specification of Molecular Chirality", *Angew. Chem. Inter. Edit.*, vol. 5, No. 4, pp. 385-415, (1966).

Cahn et al., "Specification of Configuration about Quadricovalent Asymmetric Atoms", *J Chem. Soc.*, pp. 612-622, (1951).

Cahn et al., "The Specification of Asymmetric Configuration in Organic Chemistry", *Experientia*, vol. 12, pp. 81-94, (1956).

Cahn, "An Introduction to the Sequence Rule. A system for the specification of absolute configuration", *Journal of Chemical Education*, vol. 41, No. 3, pp. 116-125, (1964).

DaSilv A, et al., "Novel Palladium-Catalyzed Oxidative Intramolecular Cyclization of β-Citronellol with H2O2: A Green and Selective Process to Synthesize Oxocine," *Catalysis Letters*, vol. 147, No. 7, 7 pages (2017), Abstract Only.

(Continued)

*Primary Examiner* — Brian Gulledge
(74) *Attorney, Agent, or Firm* — Hoxie & Associates LLC

(57) ABSTRACT

The invention relates to cosmetic compositions comprising certain polyethers, polyether derivatives (e.g., polymeric alcohols and derivatives thereof), and methods of making and using the same, specifically in the field of cosmetic or personal care compositions applied to the skin or the hair.

22 Claims, No Drawings

(56) References Cited

FOREIGN PATENT DOCUMENTS

| WO | WO-2019028053 A1 * | 2/2019 | ............. C08G 65/00 |
| WO | WO 2021/133994 | 7/2021 | |

OTHER PUBLICATIONS

Desaubry, et al., "Toward Higher Polyprenols Under 'Prebiotic' Conditions," *Tetrahedron Letters*, Issue 44, pp. 6959-6961, (2003); DOI: 10.1016/S0040-4039(03)01624-1.

Hanson, "Chiral Acylic Synthetic Intermediates from Readily Available Monoterpenoids," *Journal of Chemical Research*, vol. 39, pp. 617-621, (2015).

Ireland, et al., "The Claisen Rearrangement of N-Allylketene O,N-Acetals," *J.Org.Chem.*, vol. 39, No. 3, pp. 421-424, (1974).

Nagai, "The Formation of Ethers from dl-Citronellol in the Presence of Boron Trifluoride Etherate", *Bull. Chem. Soc. Jap.*, vol. 49, pp. 265-269, (1976).

Nagai, et al., "The Formation of Ethers from Unsaturated Aliphatic Alcohols in the Presence of Boron Trifluoride Etherate," *Bulletin of the Chemical Society of Japan*, vol. 51, No. 11, pp. 3273-3276, (1978).

PubChem CID 13469549, 11 pages, (2007); retrieved on Sep. 10, 2018 from http://pubchem.ncbi.nlm.nih.gov/compound/013469549#section=Top>.

Paroul et al. "Solvent-Free Production of Bioflavors by Enzymatic Esterification of Citronella (*Cymbopogon winterianus*) Essential Oil", *Applied Biochemistry and Biotechnology*. vol. 166, pp. 13-21, (2012); Abstract only.

Rashid, et al., "Enzymatic Synthesis of Citronellyl Palmitate in Organic Media: Process Optimization and Kinetic Evaluation," *Asian Journal of Chemistry*, vol. 28, No. 2, pp. 298-300, (2016); http://dx.doi.org/10.14233/ajchem.2016.19276.

Takahashi, et al., "Cationic Polymerization Behavior of Alkoxyallenes," *Macromolecules*, vol. 28, No. 4, pp. 866-869, (1995).

Worzakowska, "Synthesis, Characterization, and Thermal Properties of New Flavor Compounds," *J Therm Anal Calorim*, vol. 116, pp. 727-736, (2014); DOI: 10.1007/s10973-013-3541-1.

Worzakowska, "Thermal Properties of Neryl Long-Chain Esters Obtained Under Microwave Irradiation," *J. Therm Anal Calorim*, vol. 120, pp. 1715-1722, (2015); DOI: 10.1007/s10973.015-4489-0.

Written Opinion for International Application No. PCT/US2018/044657, dated Sep. 25, 2018, 7 pages.

Paroul et al., "Solvent-Free Production of Bioflavors by Enzymatic Esterification of Citronella (*Cymbopogon winterianus*) Essential Oil," Applied Biochemistry and Biotechnology, vol. 166, p. 13-21, (2012); Abstract only.

Swift et al., "Catalytic Transformations of the Major Terpene Feedstocks," Topics in Catalysis, vol. 27, No. 1-4, p. 143-155, (2004).

* cited by examiner

COSMETIC COMPOSITIONS COMPRISING POLYETHER POLYMERS

CROSS-REFERENCE TO RELATED APPLICATIONS

This application is a U.S. non-provisional application filed under 35 U.S.C. 111(a), which claims priority to, and the benefit of, U.S. Provisional Application No. 63/125,859, filed on Dec. 15, 2020, U.S. Provisional Application No. 63/092,412, filed on Oct. 15, 2020, U.S. Provisional Application No. 63/043,255, filed on Jun. 24, 2020, and U.S. Provisional Application No. 62/985,400, filed on Mar. 5, 2020, the contents of each of which are hereby incorporated by reference in their entireties.

FIELD

The invention relates to cosmetic compositions comprising certain polyethers, polyether derivatives (e.g., polymeric alcohols and derivatives thereof), and methods of making and using the same, specifically in the field of cosmetic or personal care compositions applied to the skin or the hair. The monomeric precursors of said polymers include, for example, such compounds as citronellol, prenol, isocitronellol and isoprenol.

BACKGROUND

Personal care compositions are compositions suitable for topical application to the human body, such as the skin and hair, for improving appearance and/or cleanliness. Examples of personal care compositions include skin care products (e.g., facial creams, moisturizers, face and body lotions, sunscreens, foundation, mascara, eye-liner, lipsticks, liquid soaps, solid soaps, body washes, cleansers, and the like) and hair care products (e.g., shampoos, conditioners, styling gels and hairsprays). These compositions are often intended to clean and/or to moisturize the skin and hair, and keep them in a smooth condition.

Personal care compositions must be carefully formulated to provide maximum wear and effect, and to avoid incompatibilities between ingredients which can affect stability, storability, and appearance.

Liquid polymers, such as polyethylene glycols, mixed glycol polymers, poloxamers, and silicone polymers, have important utility in cosmetic and personal care applications. For example, they can be used as emulsifiers, preservatives, stabilizers, fragrance carriers, fragrance retention agents, fragrance fixers, anti-malodor agents, anti-foaming agents, lubricants, emollients, surfactants, or as protective barriers for skin healing and UV protection, and as a substitute for petroleum-based white oil (a mixture of alkanes and cycloalkanes).

There is a need for new liquid polymer materials which can be produced in a facile manner, be easily derivatized to modify functions and properties, and preferably be made from safe and sustainable raw materials.

Citronellol, prenol, isocitronellol and isoprenol are all naturally occurring molecules that are also commercially available on a large scale. However, these molecules possess an under-utilized combination of functionalities that allow them to be polymerized and functionalized: an isobutylenic group and an alcohol.

WO 2019/028053 discloses novel polymers derived from the naturally occurring and commercially available monomers citronellol, prenol, isocitronellol and isoprenol. These monomers were effectively polymerized in a controlled way to yield a number of well-characterized polymeric ether alcohols. In addition, as these polymers as initially formed may possess primary alcohol functional groups, WO 2019/028053 further discloses functionalization of the alcohol to derive various ether, ester and other derivative products. According to the nature of functionalization, physical properties (e.g., density, surface tension, refractive index, solubility, viscosity, hydrophilicity, hydrophobicity, etc.) of these polymers can be tuned appropriately for specific applications.

The present disclosure provides new formulations for personal care compositions comprising these polyether polymers, such as, as replacement for silicone polymers or other ethereal polymers in such compositions.

BRIEF SUMMARY

In a surprising advancement in polymer science, the inventors' prior publications US 2017/0283553, and WO2019/028053, and international application PCT/US2020/66978, the contents of each of which are incorporated herein by reference, have taught generally how to prepare polyether polymers and derivatives thereof. These polyethers represent an advance in liquid polymer technology and carry with them many desirable benefits for commercial fields of application.

The present disclosure builds on the inventors' prior work by providing new personal care compositions comprising such polymers.

The present disclosure provides personal care compositions including, but not limited to, soaps (liquid or solid), body washes, skin and hair cleansers, skin creams and lotions (e.g., facial creams and lotions, face oils, eye cream, other anti-wrinkle products), ointments, sunscreens, moisturizers, hair shampoos and/or conditioners, deodorants, antiperspirants, other conditioning products for the hair, skin, and nails (e.g., shampoos, conditioners, hair sprays, hair styling gel, hair mousse), decorative cosmetics (e.g., nail polish, eye liner, mascara, lipstick, foundation, concealer, blush, bronzer, eye shadow, lip liner, lip balm) and dermocosmetics.

In some embodiments, the personal care compositions may include organically-sourced ingredients, vegan ingredients, gluten-free ingredients, environmentally-friendly ingredients, natural ingredients (e.g. soy oil, beeswax, rosemary oil, vitamin E, coconut oil, herbal oils etc.), comedogenic ingredients, natural occlusive plant based ingredients (e.g. cocoa, shea, mango butter), non-comedogenic ingredients, bakuchiol (a plant derived compound used as a less-irritating, natural alternative to retinol), color active ingredients (e.g., pigments and dyes); therapeutically-active ingredients (e.g., vitamins, alpha hydroxy acids, corticosteroids, amino acids, collagen, retinoids, antimicrobial compounds), sunscreen ingredients and/or UV absorbing compounds, reflective compounds, oils (such as castor oil and olive oil, or high-viscosity oils), film formers, high molecular weight esters, antiperspirant active ingredients, glycol solutions, water, alcohols, emulsifiers, gellants, emollients, water, polymers, hydrocarbons, conditioning agents, and/or aliphatic esters.

In a first aspect, the present disclosure provides a personal care composition comprising a compound according to Formula I below:

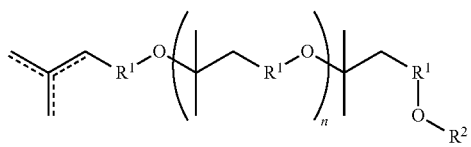

wherein $R^1$ is optionally substituted $C_1$-$C_{12}$ alkyl; $R^2$ is H, $C_{1-20}$alkyl, aryl, aryl-$C_{1-2}$ alkyl, optionally unsaturated alkyl esters or aryl esters, or $R^2$ is a moiety:

Formula I

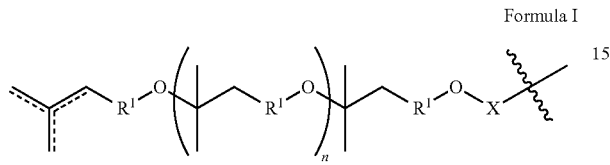

wherein X is a diacyl moiety of formula —C(O)—$R^3$—C(O)—, wherein $R^3$ is optionally substituted $C_{1-22}$ alkyl, optionally substituted $C_{2-22}$ alkenyl or optionally substituted aryl; and wherein n is an integer between 0 and 20.

In some embodiments, n is an integer between 0 and 10 (e.g., 0 to 4).

In some embodiments, the personal care composition comprises a mixture of compounds according to Formula I, for example, a mixture of compounds that only vary in the integer n. In some embodiments, the mixture of compounds according to Formula I have a number average or weight average molecular weight, optionally exclusive of the group $R^2$, of 150 to 2000 Daltons (e.g., 300 to 800 Daltons), and/or a polydispersity ($M_w/M_n$) in the range of 1 to 5 (optionally without taking into account the group $R^2$).

It is understood that ═══ represents an optional double bond (i.e., either a single or double bond), and thus that the terminal group,

may have any one of the three indicated optional bonds present (i.e., a double bond) or all optional bonds absent (i.e., all single bonds).

In further embodiments, the present disclosure provides methods of making and/or using the personal care compositions.

DETAILED DESCRIPTION

In a first aspect, the present disclosure provides a personal care composition (Composition 1) comprising a compound according to Formula I, as defined herein above. In further embodiments of the first aspect, the present disclosure provides:

1.1 Composition 1, wherein in the compound of Formula I, $R^1$ is optionally substituted linear $C_1$-$C_{12}$ alkyl or optionally substituted branched $C_1$-$C_{12}$ alkyl.
1.2 Composition 1, wherein in the compound of Formula I, $R^1$ is unsubstituted linear $C_1$-$C_{12}$ alkyl or unsubstituted branched $C_3$-$C_{12}$ alkyl.
1.3 Composition 1, wherein in the compound of Formula I, $R^1$ is unsubstituted linear $C_1$-$C_{12}$ alkyl.
1.4 Composition 1, wherein in the compound of Formula I, $R^1$ is unsubstituted branched $C_3$-$C_{12}$ alkyl.
1.5 Composition 1, wherein in the compound of Formula I, $R^1$ is $CH_2$.
1.6 Composition 1, wherein in the compound of Formula I, $R^1$ is unsubstituted branched or linear $C_6$ alkyl.
1.7 Composition 1, wherein in the compound of Formula I, $R^1$ is $CH_2CH_2CH(CH_3)CH_2CH_2$.
1.8 Composition 1 or any of 1.1-1.7, wherein in the compound of Formula I, $R^2$ is H.
1.9 Composition 1 or any of 1.1-1.7, wherein in the compound of Formula I, $R^2$ is alkyl (e.g., lower alkyl (e.g., $C_{1-6}$), or $C_{1-12}$).
1.10 Composition 1 or any of 1.1-1.7, wherein in the compound of Formula I, $R^2$ is selected from methyl, ethyl, propyl, isopropyl, n-butyl, isobutyl, sec-butyl, tert-butyl, n-pentyl, n-hexyl, n-octyl, or n-decyl.
1.11 Composition 1 or any of 1.1-1.7, wherein in the compound of Formula I, $R^2$ is aryl$C_{1-2}$ alkyl (e.g., benzyl or phenethyl).
1.12 Composition 1 or any of 1.1-1.7, wherein in the compound of Formula I, $R^2$ is aryl (e.g., phenyl).
1.13 Composition 1 or any of 1.1-1.7, wherein in the compound of Formula I, $R^2$ is an optionally unsaturated alkyl ester (e.g., C(O)—$C_{1-20}$ alkyl, or C(O)—$C_{1-6}$ alkyl).
1.14 Composition 1 or any of 1.1-1.7, wherein in the compound of Formula I, $R^2$ is C(O)—$C_{1-6}$ alkyl, optionally wherein $R^2$ is C(O)—$C_{1-5}$ alkyl, C(O)—$C_{1-4}$ alkyl, C(O)—$C_{1-3}$ alkyl or C(O)—$C_{1-2}$ alkyl.
1.15 Composition 1 or any of 1.1-1.7, wherein in the compound of Formula I, $R^2$ is C(O)—$C_{1-6}$ alkyl and said $C_{1-6}$ alkyl is selected from methyl, ethyl, propyl, isopropyl, n-butyl, isobutyl, sec-butyl, tert-butyl, n-pentyl, or n-hexyl.
1.16 Composition 1 or any of 1.1-1.7, wherein in the compound of Formula I, $R^2$ is optionally unsaturated C(O)—$C_{7-20}$ alkyl, optionally wherein $R^2$ is optionally unsaturated C(O)—$C_{10-20}$ alkyl, C(O)—$C_{12-20}$ alkyl, C(O)—$C_{14-20}$ alkyl or C(O)—$C_{16-18}$ alkyl, or C(O)—$C_{17}$ alkyl.
1.17 Composition 1 or any of 1.1-1.7, wherein in the compound of Formula I, $R^2$ is mono-unsaturated C(O)—$C_{7-20}$ alkyl, optionally wherein $R^2$ is mono-unsaturated C(O)—$C_{10-20}$ alkyl, C(O)—$C_{12-20}$ alkyl, C(O)—$C_{14-20}$ alkyl or C(O)—$C_{16-18}$ alkyl, or C(O)—$C_{17}$ alkyl (e.g., oleoyl).
1.18 Composition 1 or any of 1.1-1.7, wherein in the compound of Formula I, $R^2$ is saturated C(O)—$C_{7-20}$ alkyl, optionally wherein $R^2$ is saturated C(O)—$C_{10-20}$ alkyl, C(O)—$C_{12-20}$ alkyl, C(O)—$C_{14-20}$ alkyl or C(O)—$C_{16-18}$ alkyl, or C(O)—$C_{17}$ alkyl.
1.19 Composition 1 or any of 1.1-1.18, wherein in the compound of Formula I, wherein the $R^2$ substituent is a fatty acyl chain.
1.20 Composition 1 or any of 1.1-1.7, wherein in the compound of Formula I, $R^2$ is an aryl ester (e.g., C(O)-aryl), for example, benzoyl.
1.21 Composition 1 or any of 1.1-1.18, wherein in the compound of Formula I, the $R^2$ substituent further comprises a cationic or anionic moiety (e.g., wherein $R^2$ is alkyl, aryl, alkyl ester, or aryl ester wherein said alkyl or aryl is substituted with a cationic (e.g., quaternary ammonium) or anionic (e.g., carboxylic acid or sulfonic acid) moiety.
1.22 Composition 1 or any of 1.1-1.18, wherein in the compound of Formula I, $R^2$ is a polyether moiety, e.g., wherein the $R^2$ substituent comprises a polyethylene glycol chain.

1.23 Composition 1 or any of 1.1 et seq., wherein in the compound of Formula I, n is 0 to 10 (e.g., 1 to 9, or 2 to 8, or 1 to 7, or 2 to 6, or 1 to 5, or 2 to 4, etc.).
1.24 Composition 1 or any of 1.1 et seq., wherein in the compound of Formula I, n is 0 to 8 (e.g., 1 to 8, or 2 to 8, or 1 to 7, or 2 to 6, or 1 to 5, or 2 to 4, etc.).
1.25 Composition 1 or any of 1.1 et seq., wherein in the compound of Formula I, n is 0 to 6 (e.g., 1 to 6, or 2 to 6, or 1 to 5, or 2 to 5, or 1 to 4, or 2 to 4, etc.).
1.26 Composition 1 or any of 1.1 et seq., wherein in the compound of Formula I, n is 0 to 4 (e.g., 1 to 4, or 2 to 4, or 0 to 3, or 1 to 3, or 2 to 3, or 0 to 1, or 1 to 1, or 0 to 1).
1.27 Composition 1 or any of 1.1 et seq., wherein in the compound of Formula I, n is 0, 1, 2, 3, or 4.
1.28 Composition 1 or any of 1.1 et seq., wherein in the compound of Formula I, n is 0, 1 or 2.
1.29 Composition 1 or any of 1.1 et seq., wherein in the compound of Formula I, $R^1$ is $CH_2CH_2CH(CH_3)CH_2CH_2$, n is 0-3 (e.g., 0-2, 1-3, or 1-2) and $R^2$ is H or an optionally unsaturated alkyl ester (e.g., C(O)—$C_{1-20}$ alkyl, or C(O)—$C_{1-6}$ alkyl).
1.30 Composition 1.29, wherein in the compound of Formula I, $R^2$ is C(O)—$C_{1-6}$ alkyl and said $C_{1-6}$ alkyl is selected from methyl, ethyl, propyl, isopropyl, n-butyl, isobutyl, sec-butyl, tert-butyl, n-pentyl, or n-hexyl.
1.31 Composition 1.29, wherein in the compound of Formula I, $R^2$ is mono-unsaturated C(O)—$C_{7\text{-}20}$ alkyl, optionally wherein $R^2$ is mono-unsaturated C(O)—$C_{10\text{-}20}$ alkyl, C(O)—$C_{12\text{-}20}$ alkyl, C(O)—$C_{14\text{-}20}$ alkyl or C(O)—$C_{16\text{-}18}$ alkyl, or C(O)—$C_{17}$ alkyl (e.g., oleoyl).
1.32 Composition 1, or any of 1.1 et seq., wherein in the compound of Formula I, $R^2$ is an anti-aging moiety, UV-absorbing moiety, anti-oxidant moiety, hydrophobic (lipophilic) moiety, or hydrophilic moiety, as described herein.
1.33 Composition 1 or any of 1.1 et seq., wherein in the compound of Formula I, $R^2$ is not H, e.g., $R^2$ is alkyl (e.g., lower alkyl (e.g., $C_{1-6}$ alkyl), or $C_{1-12}$ alkyl), aryl (e.g., phenyl), $C_1$-$C_2$ alkylaryl (e.g., benzyl), optionally unsaturated alkyl esters (e.g., C(O)—$C_{1-20}$ alkyl), or aryl esters (e.g., C(O)-aryl), and further embodiments of $R^2$ as described hereinabove.
1.34 Composition 1 or any of 1.1 et seq., wherein in the compound of Formula I, the terminal group

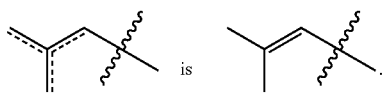 is 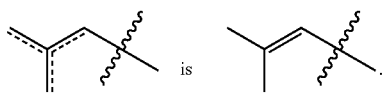.

1.35 Composition 1 or any of 1.1 et seq., wherein in the compound of Formula I, the terminal group

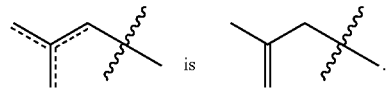

1.36 Composition 1 or any of 1.1 et seq., wherein in the compound of Formula I, the terminal group

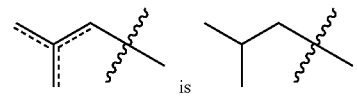

1.37 Composition 1 or any of 1.1 et seq., wherein in the compound of Formula I, the Compound of Formula I is:

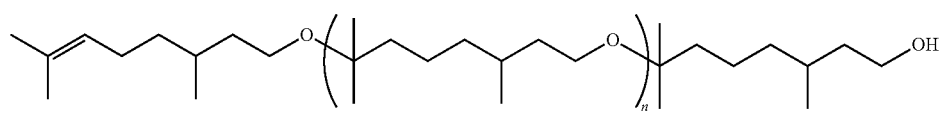

where n: 0-20 (e.g., 0-10, 1-9, 1-7, 1-4, 1-3, 0-5, 0-4, 0-3, 0, 1, 2, 3, 4, or 5).

1.38 Composition 1 or any of 1.1 et seq., wherein the Compound of Formula I is:

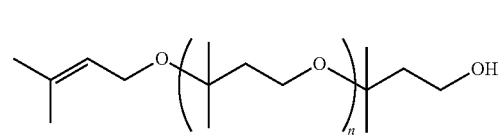

where n: 0-20 (e.g., 0-10, 1-9, 1-7, 1-4, 1-3, 0-5, 0-4, 0-3, 0, 1, 2, 3, 4, or 5).

1.39 Composition 1 or any of 1.1 et seq., wherein the Compound of Formula I is:

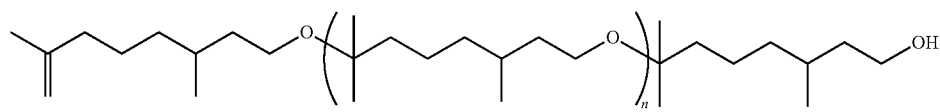

where n: 0-20 (e.g., 0-10, 1-9, 1-7, 1-4, 1-3, 0-5, 0-4, 0-3, 0, 1, 2, 3, 4, or 5).

1.40 Composition 1 or any of 1.1 et seq., wherein the Compound of Formula I is

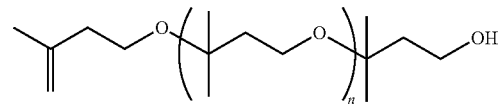

where n: 0-20 (e.g., 0-10, 1-9, 1-7, 1-4, 1-3, 0-5, 0-4, 0-3, 0, 1, 2, 3, 4, or 5).

1.41 Composition 1 or any of 1.1 et seq., wherein the Compound of Formula I is:

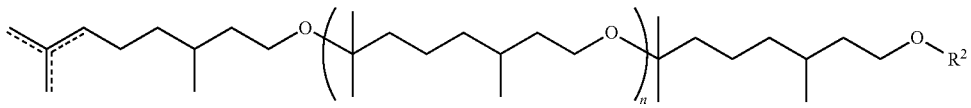

where n: 0-20 (e.g., 0-10, 1-9, 1-7, 1-4, 1-3, 0-5, 0-4, 0-3, 0, 1, 2, 3, 4, or 5), and wherein $R^2$ is as defined in any preceding embodiment.

1.42 Composition 1 or any of 1.1 et seq., wherein the Compound of Formula I is:

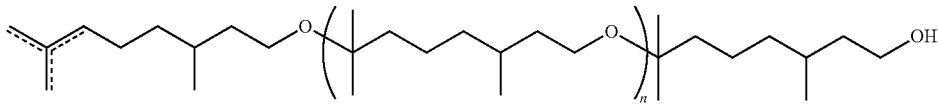

where n: 0-20 (e.g., 0-10, 1-9, 1-7, 1-4, 1-3, 0-5, 0-4, 0-3, 0, 1, 2, 3, 4, or 5).

1.43 Composition 1 or any of 1.1 et seq., wherein the Compound of Formula I is:

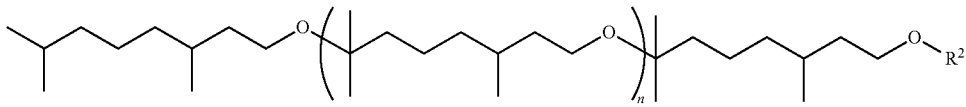

where n: 0-10 (e.g., 0-10, 1-9, 1-7, 1-4, 1-3, 0-5, 0-4, 0-3, 0, 1, 2, 3, 4, or 5), and wherein $R^2$ is as defined in any preceding embodiment, optionally wherein the Compound of Formula I is:

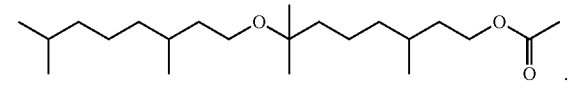 [SMILES: CC(=O)OCCC(C)CCCC(C)(C)OCCC(C)CCCC(C)C ; "."]

1.44 Composition 1 or any of 1.1 et seq., wherein the Compound of Formula I is:

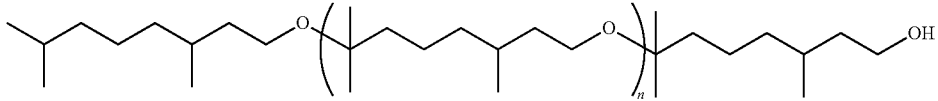

where n: 0-10 (e.g., 0-10, 1-9, 1-7, 1-4, 1-3, 0-5, 0-4, 0-3, 0, 1, 2, 3, 4, or 5), optionally wherein the Compound of Formula I is:

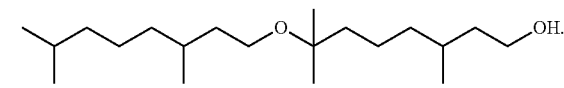 [SMILES: CC(C)CCCC(C)CCOC(C)(C)CCCC(C)CCO]

1.45 Compound 1 or any of 1.1 et seq., wherein the compound of Formula I is enantiomerically enriched, e.g., having a diastereomeric excess (e.g., an enantiomeric excess (e.e.)) of greater than 70%.

1.46 Composition 1.45, wherein the compound of Formula I has a diastereomeric excess (e.g., an enantiomeric excess (e.e.)) of greater than 80%, or greater than 85%, or greater than 90%, or greater than 95%, or greater than 97% or greater than 99%.

1.47 Composition 1.45 or 1.46, wherein each chiral carbon of the compound of Formula I, exclusive of the group $R^2$, has the (R)-configuration, optionally wherein each chiral carbon of the group $R^2$ also has the (R)-configuration.

1.48 Composition 1.45 or 1.46, wherein each chiral carbon of the compound of Formula I, exclusive of the group $R^2$, has the (S)-configuration, optionally wherein each chiral carbon of the group $R^2$ also has the (S)-configuration.

1.49 Composition 1.45 or 1.46, wherein each chiral carbon of the compound of Formula I, exclusive of the group $R^2$, has the (R)-configuration, and wherein each chiral carbon of the group $R^2$ has the (S)-configuration.

1.50 Composition 1.45 or 1.46, wherein each chiral carbon of the compound of Formula I, exclusive of the group $R^2$, has the (S)-configuration, and wherein each chiral carbon of the group $R^2$ has the (R)-configuration.

1.51 Composition 1 or any of 1.1 et seq., wherein the composition comprises a single compound of Formula I according to any one of the compounds described in Composition 1 or 1.1-1.50, the compound being present in an amount of 0.1 to 50% by weight of the composition, e.g., 0.1-40%, or 0.1-30%, or 0.1-20%, or 0.1-10%, or 0.1-5%, or 1-40%, or 1-30%, or 1-20%, or 1-10%, or 1-5%, or about 3.5%, or 5-15%, e.g., about 10%, or 30-50%, or 30-40%.

1.52 Composition 1 or any of 1.1 et seq., wherein the composition comprises one or more compounds of Formula I (e.g., from one up to ten specific compounds), wherein each compound is independently a compound described in Composition 1 or 1.1-1.50, each compound being present in an amount of 0.01 to 40% by weight of the composition, e.g., 0.01-30%, or 0.01-20%, or 0.01-10%, or 0.01-5%, or 0.01-1%, or 0.01-0.1%, or 0.1-20%, or 0.1-15%, or 0.1-10%, or 0.1-5%, or 0.1 to 1%.

1.53 Composition 1 or any of 1.1 et seq., wherein the personal care composition comprises a mixture of compounds according to Formula I.

1.54 Composition 1.53, wherein the mixture of compounds according to Formula I vary only in the integer n.

1.55 Composition 1.53 or 1.54, wherein the mixture of compounds according to Formula I have a number average molecular weight ($M_n$), optionally exclusive of the group $R^2$, of 150 to 2000 Daltons (e.g., 300 to 800 Daltons).

1.56 Composition 1.55, wherein the mixture of compounds according to Formula I have a number average molecular weight ($M_n$), optionally exclusive of the group $R^2$, of 300 to 1900 Daltons, e.g., 300 to 1600 Daltons, or 300 to 1300 Daltons, or 300 to 1100 Daltons, or 300 to 1000 Daltons, or 300 to 800 Daltons, or 300 to 700 Daltons, or 300 to 500 Daltons, or 400 to 1000 Daltons, or 400 to 700 Daltons, or 600 to 1100 Daltons, or 600 to 1000 Daltons, or 600 to 800 Daltons or about 500 Daltons, or about 414 Daltons.

1.57 Composition 1.53 or 1.54, wherein the mixture of compounds according to Formula I have a weight average molecular weight ($M_w$), optionally exclusive of the group $R^2$, of 150 to 2000 Daltons (e.g., 300 to 800 Daltons).

1.58 Composition 1.57, wherein the weight average molecular weight ($M_w$) of the compounds in the composition, optionally exclusive of the group $R^2$, is 300 to 1900 Daltons, e.g., 300 to 1600 Daltons, or 300 to 1300 Daltons, or 300 to 1100 Daltons, or 300 to 1000 Daltons, or 300 to 800 Daltons, or 300 to 700 Daltons, or 300 to 500 Daltons, or 400 to 1000 Daltons, or 400 to 700 Daltons, or 600 to 1100 Daltons, or 600 to 1000 Daltons, or 600 to 800 Daltons, or about 438 Daltons.

1.59 Any of Compositions 1.53-1.58, wherein the mixture of compounds according to Formula I have a polydispersity ($M_w/M_n$) in the range of 1 to 5 (optionally without taking into account the group $R^2$).

1.60 Composition 1.59, wherein the polydispersity ($M_w/M_n$) is in the range of 1 to 4, or 1 to 3, or 1 to 2.5, or 1 to 2, or 1 to 1.5, or about 1 to 1.25, or about 1, or 1.5 to 3.5, or 1.5 to 2.5, or about 1.5, or 2 to 4, or 2 to 3, or 2 to 2.5, or about 2, or 1 to 1.25, or 1 to 1.20, or 1 to 1.15, or 1 to 1.10, or about 1.06.

1.61 Any of Compositions 1.53-1.60, wherein the compounds of Formula I in the composition have an average n value of 0 to 8, measured either as a weight average or number average.

1.62 Any of Compositions 1.53-1.60, wherein the compounds of Formula I in the composition have an average n value of 0 to 6, measured either as a weight average or number average.

1.63 Any of Compositions 1.53-1.60, wherein the compounds of Formula I in the composition have an average n value of 0 to 5, measured either as a weight average or number average.

1.64 Any of Compositions 1.53-1.60, wherein the compounds of Formula I in the composition have an average n value of about 0, about 1, about 2, about 3, or about 4, measured either as a weight average or number average.

1.65 Any of Compositions 1.53-1.60, wherein the compounds of Formula I in the composition have an average n value of about 0, about 1 or about 2, measured either as a weight average or number average.

1.66 Composition 1.65, wherein the compounds of Formula I in the composition have an average n value of about 0.5, e.g., about 0.52, measured as the weight average.

1.67 Any of Compositions 1.53-1.66, wherein the compounds of Formula I in the compositions are all compounds of the structure:

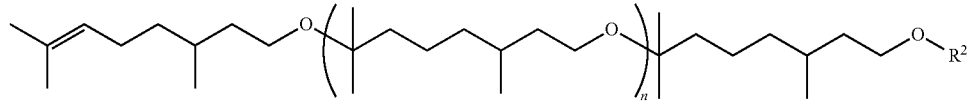

wherein $R^2$ is acetyl and n is from 0 to 8 (e.g., 0-7, 1-7, 1-4, 1-3, 0-5, 0-4, 0-3, 0, 1, 2, 3, 4, or 5).

1.68 Composition 1.67, wherein at least 95% of the compounds of Formula I by weight have an n value of 0, 1, 2 3 or 4, e.g., at least 97% or at least 98% or at least 99% of said compounds.

1.69 Composition 1.67 or 1.68, wherein at least 90% of the compounds of Formula I by weight have an n value of 0, 1 or 2, e.g., 90-98% or 95-98% of said compounds.

1.70 Composition 1.67, 1.68 or 1.69, wherein at least 70% of the compounds of Formula I by weight have an n value of 0 or 1, e.g., at least 80%, or 80-90% or 80-85% of said compounds.

1.71 Composition 1.67, 1.68, 1.69 or 1.70, wherein at least 30% of the compounds of Formula I by weight have an n value of 0, e.g., at least 40%, or 40-60% or 45-55% of said compounds.

1.72 Composition 1, or any of 1.1-1.71, wherein the one (or more) compounds of Formula I is present as an aqueous dispersion.

1.73 Composition 1, or any of 1.1-1.72, wherein the composition further comprises at least one cosmetic active (e.g., aluminum zirconium tetrachlorohydrex gly, aluminum starch octenyl succinate) or cosmetically acceptable excipient, e.g. water, diluent or carrier, liquid polymer (e.g., poloxamer, vegetable oils, cyclomethicone), surfactant (e.g., sodium lauryl sulfate, sodium laureth sulfate, polysorbate-80, polysorbate-20, polysorbate-85, cocamidopropyl betaine, polyquaternium-30), hydrotrope, emollient (e.g., propylene glycol), emulsifier (e.g., glyceryl stearate, cetyl alcohol, stearic acid), stabilizer, preservative (e.g., phenoxyethanol, DMDM hydantoin, iodopropynyl butylcarbamate, alkyl paraben), humectant (e.g., glycerol, sorbitol, xylitol, propylene glycol), rheological additive (e.g., isopropyl myristate, silica dimethyl sulfate), antioxidant (e.g., vitamin A or E, butylated hydroxytoluene [BHT], butylated hydroxyanisole [BHA]), fragrance, fragrance carrier, fragrance fixer, texturizer (e.g., silica), color or pigment (e.g., titanium dioxide, iron oxide, mica), or thickener (e.g., triglycerides), optionally wherein any one or more cosmetic actives or excipients are organically sourced and/or renewable and/or vegan.

1.74 Composition 1.73, wherein the one or more cosmetic actives or cosmetically acceptable excipients are selected from renewable plants or materials derived from renewable plants (e.g., cocoa, mango, gardenia flowers), soy oil, beeswax, rosemary oil, vitamin E, sunflower seed oil, jojoba butter, avocado oil, jojoba seed oil, grape seed oil, coconut oil, hydrogenated vegetable oil, peppermint oil, lavender oil, sandalwood oil, bergamot oil, rose oil, chamomile oil, ylang-ylang oil, tea-tree oil, jasmine oil, lemon oil, clementine oil, coriander seed oil, corn mint oil, eucalyptus lemon oil, geranium oil, ginger oil, key lime oil, basil oil, kukui nut seed oil, shea butter, hemp seed oil, hydrogenated grape seed oil, meadowfoam seed oil, mango seed butter, rice bran seed oil, rosehip fruit oil, soy lecithin, cupuacu seed butter, pumpkin seed oil, chamomile flower extract, bergamot fruit oil, palmarosa oil, lavender oil, rosemary extract, clary sage oil, cocoa butter, soybean oil, calendula flower extract, jasmine absolute, castor oil, penta-erythritol tetra-isosterate, candelilla wax, myristyl lactate, petrolatum, carnauba, ozokerite wax, cetyl esters, behenyl erucate, diisopropyl sebacate, propylene glycol stearate, corn starch, polyethylene glycol (e.g., PEG 400), polyethylene glycol laurate (e.g., PEG-400 laurate or PEG-8 laurate), myreth 3-laurate, acetamide monoethanolamine, isostearamidopropyl laurylacetodimonium chloride, ethylenediamine tetraacetic acid (e.g., EDTA disodium or tetrasodium), disodium dimethicone copolyol sulfosuccinate, triethanolamine, boron nitride, hexamethyl disiloxane, trifluoropropyl polysiloxane, glyceryl stearate, PEG-100 stearate, benzophenone-3, mineral oil, caprylic/capric triglyceride, lauryl lactate, carbomer, diazolidinyl urea, coco-glucoside, ethylene glycol distearate, D-panthenol, methyldibromo glutaronitrile, laureth-3, lactic acid, SD-Alcohol 40, bisabolol, tocopherol acetate, coco-caprylate, PEG-120 methyl glucose dioleate, cocamidopropyl hydroxy sultaine, and licorice extract, optionally wherein any preceding ingredient is organically sourced.

1.75 Composition 1, or any of 1.1-1.74, wherein the one or more Compounds of Formula I perform the function of a diluent or carrier, surfactant, emollient, stabilizer, preservative, humectant, rheological additive, antioxidant, fragrance, fragrance carrier, fragrance fixer, thickener, UV light absorber, and/or silicone or petroleum jelly replacement.

1.76 Composition 1, or any of 1.1-1.75, wherein the composition is free of any surfactant (other than any compound of Formula I).

1.77 Composition 1, or any of 1.1-1.76, wherein the composition is free of any emulsifier (other than any compound of Formula I).

1.78 Composition 1, or any of 1.1-1.77, wherein the composition is free of any emollient (other than any compound of Formula I).

1.79 Composition 1, or any of 1.1-1.78, wherein the composition is free of any humectant (other than any compound of Formula I).

1.80 Composition 1, or any of 1.1-1.79, wherein the composition is free of any preservative (other than any compound of Formula I).

1.81 Composition 1, or any of 1.1-1.80, wherein the composition is free of any stabilizer (other than any compound of Formula I).

1.82 Composition 1, or any of 1.1-1.81, wherein the composition is free of any rheological additive (other than any compound of Formula I).

1.83 Composition 1, or any of 1.1-1.82, wherein the composition is free of any antioxidant (other than any compound of Formula I).

1.84 Composition 1, or any of 1.1-1.83, wherein the composition is free of any thickener (other than any compound of Formula I).

1.85 Composition 1, or any of 1.1-1.84, wherein the composition comprises less than 10% by weight of any silicone polymer, e.g., less than 5%, or less than 1%, or less than 0.1% or less than 0.09%.

1.86 Composition 1, or any of 1.1-1.85, wherein the composition is free of any silicone polymer.

1.87 Composition 1, or any of 1.1-1.86, wherein the composition further comprises a meroterpene (e.g., bakuchiol).

1.88 Composition 1, or any of 1.1-1.86, wherein the composition further comprises at least one water-soluble cyclodextrin or water-soluble metallic salt (e.g., a zinc or copper salt) as a malodor-counteracting agent.

1.89 Composition 1, or any of 1.1-1.88, wherein the composition is a toothpaste, mouthwash, soap (liquid or solid), body wash, skin cleanser, hair cleanser, skin cream or skin lotion (e.g., facial cream or lotion, face oil, eye cream, other anti-wrinkle products), ointment, sunscreen, moisturizer, hair shampoo and/or conditioner, deodorant, antiperspirant, other conditioning product for the hair, skin, and nails (e.g., shampoo, conditioner, hair spray, hair styling gel, hair mousse), decorative cosmetic (e.g., nail polish, eye liner, mascara, lipstick, foundation, concealer, blush, bronzer, eye shadow, lip liner, or lip balm) or a dermocosmetic.

1.90 Composition 1, or any of 1.1-1.89, wherein the composition is gluten free.

1.91 Composition 1, or any of 1.1-1.89, wherein the composition is a water-in-oil emulsion.

1.92 Composition 1, or any of 1.1-1.89, wherein the composition is an oil-in-water emulsion.

1.93 Composition I, or any of 1.1-1.92, wherein the composition further comprises one or more hydrocarbons.

1.94 Composition 1.93, wherein the hydrocarbons comprise linear or branched aliphatic hydrocarbons having from 7 to 30 carbon atoms, e.g., 7 to 25 carbon atoms, or 7 to 23 carbon atoms, or 7 to 12 carbon atoms, or 12 to 15 carbon atoms, or 15 to 18 carbon atoms, or 18 to 21 carbon atoms, or 21 to 23 carbon atoms, or 23 to 28 carbon atoms, or any combination thereof.

1.95 Composition 1.93, wherein the hydrocarbons comprise branched or unbranched cyclic aliphatic hydrocarbons having from 5 to 20 carbon atoms, e.g., 5 to 16 carbon atoms, or 5 to 12 carbon atoms, or 5 to 10 carbon atoms, or 5 to 8 carbon atoms, or 8 to 10 carbon atoms, or 10 to 12 carbon atoms, or 12 to 16 carbon atoms, or 16 to 20 carbon atoms, or any combination thereof.

1.96 Any one of Compositions 1.93-1.95, wherein the hydrocarbons comprise saturated hydrocarbons, monounsaturated hydrocarbons, polyunsaturated hydrocarbons, or some combination thereof.

1.97 Any one of Compositions 1.93-1.96, wherein the hydrocarbons do not comprise aromatic hydrocarbons, and/or do not comprise cyclic hydrocarbons, e.g., wherein the composition does not comprise aromatic hydrocarbons and/or cyclic hydrocarbons.

1.98 Any one of Compositions 1.93-1.97, wherein the one or more hydrocarbons are selected from heptane, octane, nonane, decane, undecane, dodecane, isododecane, tridecane, tetradecane, pentadecane, hexadecane, heptadecane, octadecane, nonadecane, henicosane, docosane, and tricosane, and any saturated linear or saturated branched isomer thereof.

1.99 Composition 1.98, wherein the one or more hydrocarbons are selected from undecane, tridecane, or a mixture thereof.

It is understood that the compositions according to Composition 1 et seq., described herein, may comprise a mixture of discrete polymers according to Formula I which vary in the precise value of the integer n. Thus, in some embodiments, the Composition 1 et seq. may comprise only a single polymer according to Formula I (with particular groups $R^1$ and $R^2$) having a single value for the integer n. In other embodiments, the Composition 1 et seq. is understood to comprise a mixture of compounds of Formula I (with particular groups $R^1$ and $R^2$) having different values for the integer n, e.g., at least two different compounds of Formula I having different values for the integer n (for example, a mixture which comprises a compound of Formula I wherein n is 0, and a compound of Formula I wherein n is 1). Typically, in such compositions, substantially all polymers according to Formula I in the composition will have the same groups $R^1$ and $R^2$, that is, the various polymers according to Formula I in the composition will differ only in the value of the integer n. As used in the preceding sentence (and analogously elsewhere herein), the term "substantially all polymers according to Formula I" is understood to recognize that minor synthetic impurities may be present in which $R^1$ and/or $R^2$ differ from that of the bulk of the composition (e.g., owing to minor impurities in starting materials, minor side-products in the synthesis, or minor amounts of unreacted intermediates, which may be present despite efforts at purification). Any of the aforementioned compositions may further comprise any one or more cosmetically acceptable ingredients.

"Cosmetically acceptable ingredients" refers to materials used in personal care compositions without any toxic effect when present in the amounts usually found in personal care compositions are not envisioned as part of the present invention.

In some embodiments, the compound of Formula I is used as diluent to provide a composition having a thin, smooth skin feel and useful for quick dry applications.

In some embodiments, the compound of Formula I is used to provide a long-lasting, durable, high resistance, low viscosity and/or easy to use film forming effect.

In some embodiments, the compound of Formula I is used as aid in spreadability, skin breathability and in lubrication in combination.

In some embodiments, the compound of Formula I is used as a "non-comedogenic" or "non-occlusive" ingredient in a natural alternative to Vaseline or petroleum ointments. The term "non-comedogenic" used to describe ingredients or products that does not clog pores.

In some embodiments, cosmetic compositions utilize the compound of Formula I as a substitute for petroleum jelly, for example, in combination with one or more natural ingredients such as soy oil, beeswax, rosemary oil, or vitamin E.

In some embodiments, the present disclosure provides a cosmetic compositions as a natural alternative to Vaseline or petroleum ointment, where the compound of Formula I is used in combination with one or more natural occlusive ingredients, such as, but not limited to, sunflower seed oil, jojoba butter, avocado oil, jojoba seed oil, grape seed oil, coconut oil, hydrogenated vegetable oil, kukuinut seed oil, shea butter, hemp seed oil, hydrogenated grape seed oil, meadowfoam seed oil, mango seed butter, rice bran seed oil, rosehip fruit oil, soy lecithin, cupuacu seed butter, pumpkin seed oil, chamomile flower extract, bergamot fruit oil, palmarosa oil, lavender oil, beeswax, rosemary extract, clary sage oil, cocoa butter, soybean oil, calendula flower extract, jasmine absolute, gardenia flowers to nourish and moist skin without being super greasy. This type of natural personal care product can be used on hands, feet, body and even as a gentle makeup remover.

In some embodiments, the present disclosure provides a cosmetic composition which is a balm, comprising the compound of Formula I in combination with raw ingredients such as, but not limited to, organic coconut oil, organic cocoa butter, organic jojoba oil and organic sweet almond oil.

In some embodiments, the present disclosure provides compositions comprising a compound of Formula I combined with essential oils such as, but not limited to, peppermint oil, lavender oil, sandalwood oil, bergamot oil, rose oil, chamomile oil, ylang-ylang oil, tea-tree oil, jasmine oil, lemon oil, clementine oil, coriander seed oil, corn mint oil, eucalyptus lemon oil, geranium oil, ginger oil, key lime oil, basil oil in the practice of aromatherapy, a form of alternative medicine. The resulting compositions may be inhaled or applied to skin through various methods.

In some embodiments, the compound of Formula I is combined with at least one hydrotrope or renewable hydrotrope. The term "hydrotrope" refers to compounds capable of solubilizing hydrophobic compounds (such as the compound of Formula I) in aqueous solution (by means other than micellar solubilization). The term "renewable hydrotropes" refers compounds that are obtained from renewable or sustainable sources.

In some embodiments, the present disclosure provides cosmetic compositions comprising the compound of Formula I in combination with a meroterpene, such as bakuchiol. The term "meroterpene" refers to compounds with a partial terpenoid structure. Meroterpenes are less-irritating, gentle, vegan ingredients and are natural alternatives to retinol in skin-care formulas.

In some embodiments, the present disclosure provides "concentrated cosmetic compositions" wherein the compound of Formula I can be used in high concentration with different surfactants of varying ionicities to form effective cleansing compositions with unique rheological properties.

In some embodiments, the present disclosure provides "concentrated cosmetic compositions" wherein the compound of Formula I can be used with a variety of highly concentrated surfactants of differing ionicities to form effective cleansing compositions with unique rheological properties.

Methods to make these ethers similar those described herein are described in US2017/0283553 and WO2019/028053, the contents of which are incorporated by reference herein in their entireties. Such polymers can generally be made with high degrees of polymerization in a short period of time by using a resin-bound acid catalyst, such as Amberlyst®, under neat, solvent-free conditions. Amberlyst-type resins are recognized in the art and understood to be macroreticular or cellular resins covalently bonded to sulfonic acid or carboxylic acid groups, preferably sulfonic acid groups. Such polymerizations can be done at or below room temperature, preferably at slightly elevated temperature, between 30 and 110° C., or even more preferably between 40 and 90° C. (e.g., about 50° C.). Such polymerizations can take place in batch reactors, semi-batch reactors, or even more preferably in continuous packed bed-type reactors of the type described in International Application PCT/US2017/50808, the contents of each of which are incorporated herein by reference.

Other aspects regarding the use of compounds and compositions of the present disclosure may be found as disclosed in US2017/0283553 and WO2019/028053, the contents of which are incorporated by reference herein in their entireties.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore, as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

In some formulae of the present application, one or more chiral centers are identified by an asterisk placed next to the chiral carbon. In other formulae, no chiral center is identified, but the chiral isomers are nonetheless covered by these formulae.

Some compounds of the present invention can exist in a tautomeric form which is also intended to be encompassed within the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group having from 1 to 22 carbon atoms, typically although, not necessarily, containing 1 to about 12 carbon atoms, such as methyl, ethyl, n-propyl, isopropyl, n-butyl, isobutyl, t-butyl, octyl, and the like.

As used herein throughout, the term "unsaturated alkyl" is understood as being the same as "alkenyl." Thus, the term "optionally unsaturated alkyl ester" refers to an ester having either an alkyl chain or an alkenyl chain. Thus, in this context, "optionally unsaturated alkyl ester" is equivalent to the "alkyl ester or alkenyl ester." As a result, term such as "$R^2$ is an optionally unsaturated alkyl ester (e.g., C(O)—$C_{1-20}$ alkyl, or C(O)—$C_{1-6}$ alkyl)" are understood to indicate as exemplary esters, both C(O)—$C_{1-20}$ alkyl and C(O)—$C_{1-6}$ alkyl, as well as C(O)—$C_{2-20}$ alkenyl and C(O)—$C_{2-6}$ alkenyl. Likewise, the term "$R^2$ is mono-unsaturated C(O)—$C_{7-20}$ alkyl" is understood as the same as "$R^2$ is mono-unsaturated C(O)—$C_{7-20}$ alkenyl".

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like.

The term "aryl" as used herein refers to an aromatic hydrocarbon moiety comprising at least one aromatic ring of 5-6 carbon atoms, including, for example, an aromatic hydrocarbon having two fused rings and 10 carbon atoms (i.e., naphthalene).

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

The terms "branched" and "linear" (or "unbranched") when used in reference to, for example, an alkyl moiety of $C_a$ to $C_b$ carbon atoms, applies to those carbon atoms defining the alkyl moiety. For example, for a $C_4$ alkyl moiety, a branched embodiment thereof would include an isobutyl, whereas an unbranched embodiment thereof would be an n-butyl. However, an isobutyl would also qualify as a linear $C_3$ alkyl moiety (a propyl) itself substituted by a $C_1$ alkyl (a methyl).

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-Cao arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

Where a range is recited, such as 0-10 or 1-7, the range embraces all integer values within the range, as well as integer subranges. Thus, the range 0-10 includes 0-9, 0-8, 0-7, 0-6, 0-5, 0-4, 0-3, 0-2, 1-10, 1-9, 1-8, 1-7, 1-6, 1-5, 1-4, 1-3, 1-2, 1-9, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 4-4, 4-3, 5-10, 5-9, 5-8, 5-7, 5- 6, 6-10, 6-9, 6-8, 6-7, 7-10, 7-9, 7-8, 8-10, 8-9, 9-10, 0, 1, 2, 3, 4, 5, 6, 7, 8, 9 and 10.

All percentages used herein, unless otherwise indicated, are by volume.

All ratios used herein, unless otherwise indicated, are by molarity.

EXAMPLES

Citronellol polymers have been previously disclosed, such as, in US 2017/0283553, and WO2019/028053, and application No. 62/953,850, the contents of each of which are incorporated herein by reference. As used hereinbelow, the term "Citronellol polymers" refers to polymers having the structure:

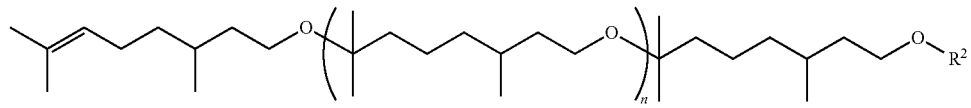

wherein $R^2$ is H or —C(O)$C_{1-6}$ alkyl (e.g., acetyl, propionyl, butyryl, isobutyryl, etc.) and n is from 0 to 8 (e.g., 0 to 4). The following examples provide exemplary compositions made according to the present disclosure.

Example 1

A moisturizing lotion is prepared using Citronellol polymer, according to the table below (percent values shown are w/w):

| Ingredient | Purpose | Lotion (control) | Lotion |
|---|---|---|---|
| Water | Diluent | 77.75% | 75.77% |
| Isopropyl myristate | Occlusive | 4.25% | 4.25% |
| Glycerin | Humectant | 5.20% | 4.00% |
| Triglyceride blend | Thickener | 4.00% | 4.00% |
| Glyceryl Stearate | Emulsifier | 4.00% | 4.00% |
| Cetyl Alcohol | Emulsifier | 2.00% | 2.00% |
| Stearic acid | Emulsifier | 2.00% | 2.00% |
| Phenoxyethanol | Preservative | 0.5% | 0.5% |
| Fragrance | Fragrance | QS | QS |
| Citronellol Polymer | Soothing agent | — | 3.5% |

Each lotion composition is prepared by first combining the water and glycerol and heating to about 70-75° C. in one beaker, and then combining the oil phases (cetyl alcohol, stearic acid, isopropyl myristate, glyceryl stearate, triglyceride blend, and Citronellol polymer) in a second beaker, and also heating to about 70-75° C. Into a plastic beaker is then successively added the hot oil phase followed by the hot water phase, and the beaker is immediately immersed in a cold water bath and the mixture is mixed at high speed with a handheld electric mixer. To the resulting homogenous emulsion at about 30-40° C. is added the preservative and fragrance with gentle mixing. Both compositions are found to have a pH of 5 to 5.5.

It is found that the control lotion is homogenous and has a slightly hard texture. After applying it to the skin, it becomes easily dried off. In contrast, it is found that the lotion composition containing Citronellol polymer has a softer, smoother feel on the skin and does not dry off.

Example 2

A concealer composition is prepared using Citronellol polymer according to the table below (percent values shown are w/w):

| Ingredient | Purpose | Concealer |
| --- | --- | --- |
| Water | Diluent | 60% |
| Isopropyl myristate | Occlusive | 5% |
| Triglyceride blend | Thickener | 10% |
| Cetyl alcohol | Emulsifier | 4% |
| Phenoxyethanol | Preservative | 0.5% |
| Fragrance | Fragrance | 0.3% |
| Citronellol polymer | Soothing agent | 10% |
| Propylene glycol | Emollient | 4% |
| Silica | Texturizer | 2% |
| Titanium dioxide | Color pigment | 3% |
| Iron Oxide | Color pigment | 1.20% |

The concealer composition is prepared by first combining the water and glycerol and heating to about 70-75° C. in one beaker, and combining the oil phases (cetyl alcohol, triglyceride blend, silica and Citronellol polymer) in a second beaker, and also heating to about 70-75° C. The titanium dioxide and iron oxide colorants are then ground together with a mortar and pestle, and then combined with the propylene glycol. The propylene glycol/colorant mixture is then added to the oil phases and mixed. Into a plastic beaker is then successively added the hot oil phase followed by the hot water phase, and the beaker is immediately immersed in a cold water bath and mixed with a spatula while cooling. This results in two-phase heterogenous mixture comprising an oil phase and a mixed oil/water emulsion.

It is found that the oil phase presents highly pigmented properties, and therefore shows very good coverage. The whole formulation is soft matte and upon application to the skin a soft, velvet feel is obtained. In comparison to a commercially available concealer, the concealer of Example 2 shows more matte than wet properties.

Example 3

A primer composition is prepared using Citronellol polymer, according to the following table (percent values shown are w/w):

| Ingredient | Purpose | Primer |
| --- | --- | --- |
| Phenoxyethanol | Preservative | 0.5% |
| Citronellol polymer | Soothing agent | 34.50% |
| Propylene glycol | Emollient | 45% |
| Silica dimethyl silylate | Gellant | 20% |

The primer composition is prepared heating the propylene glycol to 70-75° C. in a beaker, then slowly adding the silica dimethyl silylate with stirring to form a uniform gel. The Citronellol polymer is then added with stirring, followed by cooling the mixture. The preservative is then added after the mixture has cooled below 40° C. The resulting product is uniform gel with a velvet-like feel after application to the skin. Compared to a similar commercial silicone-based primer, the present primer provides a smoother and more glowy appearance on the skin.

Example 4

A natural alternative to "Vaseline or petroleum ointment" is prepared using citronellol polymer according to the table below (percent value shown are w/w)

| Ingredients | % |
| --- | --- |
| Beeswax | 5 |
| Citronellol polymer | 95 |

The natural alternative to "Vaseline or petroleum ointment" is prepared by heating a mixture of citronellol polymer and beeswax in a 50 mL glass beaker. The temperature is raised to 70-75° C. until the mixture become homogenous and clear. The composition is slowly cooled to ambient temperature to an opaque, gel-like ointment texture. The resulting mixture is soft and not heavy or overwhelming after application on skin compared to a commercial petroleum ointment.

The invention is further described in connection with the following examples which are set forth for the purpose of illustration only.

Example 5

A lipstick composition may be prepared comprising the following ingredients:

| Ingredient | wt. % |
| --- | --- |
| Castor oil | 0.1-50% |
| Mica (and) Titanium dioxide | 0.1-5% |
| FD & C Red # 40 Aluminum Lake (39%) | 0.1-4% |
| Micro Titanium dioxide | 0.1-3% |
| Pentaerythritol Tetraisostearate | 0.1-8% |
| Beeswax | 0.1-7% |
| Candelilla wax | 0.1-5% |
| Citronellol polymer (replacing mineral oil as a supple) | 0.1-50% |
| Myristyl Lactate | 0.1-3% |
| Petrolatum | 0.1-3% |
| Carnauba | 0.1-2% |
| Ozokerite wax | 0.1-2% |
| Cetyl esters | 0.1-1.5% |
| BHT | 0.1-0.05% |
| Fragrance | Q.S. |

Example 6

An antiperspirant gel may be prepared comprising the following ingredients:

| Ingredient | wt. % |
| --- | --- |
| Citronellol polymer (emulsifier) | 0.1-10% |
| Cyclomethicone (SF1204) | 0.1-14% |
| Polysorbate-80 | 0.1-0.25% |
| Aluminum Zirconium Tetrachlorohydrex Gly | 0.1-20% |
| Water | 0.1-55.75% |

Example 7

An antiperspirant stick composition may be prepared comprising the following ingredients:

| Ingredient | wt. % |
| --- | --- |
| Stearyl alcohol | 0.1-20% |
| Schercemol BE/Behenyl Erucate | 0.1-10% |

-continued

| Ingredient | wt. % |
| --- | --- |
| Diisopropyl Sebacate | 0.1-15% |
| Citronellol polymer | 0.1-15% |
| Propylene Glycol Stearate | 0.1-10% |
| Cornstarch | 0.1-10% |
| Aluminum Zirconium Tetrachlorohydrex Gly | 0.1-20% |

Example 8

A foaming bath oil composition may be prepared comprising the following ingredients:

| Ingredient | wt. % |
| --- | --- |
| Citronellol polymer (mineral oil replacement) | 0.1-20% |
| PEG 400 Monolaurate/PEG-8 Laurate | 0.1-20% |
| Schercemol Mel-3/Myreth-3 Laurate | 0.1-8% |
| Schercomid AME-100/Acetamide MEA | 0.1-8% |
| Schercoquat IALA/ Isostearamidopropyl Laurylacetodimonium Chloride | 0.1-10% |
| Water, Deionized | 0.1-29% |

Example 9

A moisturizing body wash composition may be prepared comprising the following ingredients:

| Ingredient | wt. % |
| --- | --- |
| Deionized water | 0.1-51.45% |
| Disodium EDTA | 0.1-0.05% |
| Carbomer (1) | 0.1-1% |
| Citronellol polymer derivative (Humectant) | 0.1-2% |
| Glycerin (96%) | 0.1-1% |
| Sodium Laureth Sulfate (28-30%) | 0.1-16% |
| Disodium Dimethicone Copolyol Sulfosuccinate (30%) | 0.1-15% |
| Polysorbate-20 | 0.1-1% |
| Dimethicone | 0.1-5% |
| Cocamidopropyl Betaine | 0.1-3% |
| Polyquaternium-39 | 0.1-3% |
| DMDM Hydantoin (and) Iodopropynyl Butylcarbamate | 0.1-0.15% |
| Fragrance | 0.1-0.25% |
| Triethanolamine (99%) | 0.1-1.1% |

Example 10

A sun-blocking cream composition may be prepared comprising the following ingredients:

| Ingredient | wt. % |
| --- | --- |
| Citronellol polymer | 0.1-37% |
| Iron oxide | 0.1-3.5% |
| Titanium dioxide | 0.1-20% |
| Zinc oxide | 0.1-5% |
| Boron Nitride | 0.1-8% |

-continued

| Ingredient | wt. % |
| --- | --- |
| Hexamethyl disiloxane | 0.1-10% |
| Cyclomethicone | 0.1-11.5% |
| Trifluoropropylmethyl polysiloxane | 0.1-5% |

Example 11

A daily UV protection lotion may be prepared comprising the following ingredients:

| Ingredient | wt. % |
| --- | --- |
| Octyl Dimethyl PABA | 0.1-4% |
| Glyceryl Stearate (and) PEG-100 Stearate | 0.1-3.5% |
| Benzophenone-3 | 0.1-3% |
| Titanium dioxide (and) Mineral Oil (and) Caprylic / Capric Triglyceride | 0.1-3% |
| Petrolatum/Snow petrolatum | 0.1-2% |
| Polysorbate 20 | 0.1-2% |
| Lauryl Lactate | 0.1-2% |
| Cetyl alcohol | 0.1-1% |
| Citronellol polymer | 0.1-1% |
| Deionized water | 0.1-74.65% |
| Propylene Glycol | 0.1-2.5% |
| Carbomer | 0.1-0.20% |
| Triethanolamine | 0.1-0.15% |
| Diazolidinyl Urea | 0.1-1% |

Example 12

A hair shampoo composition may be prepared comprising the following ingredients:

| Ingredient | wt. % |
| --- | --- |
| Sodium Laureth Sulphate | 0.1-28% |
| Cocamidopropylbetaine | 0.1-6% |
| Coco glucoside | 0.1-6% |
| Glycol distearate | 0.1-3% |
| D-Panthenol | 0.1-1% |
| Citronellol polymer | 0.1-50% |
| Methyldibromoglutaronitrile, Propylene Glycol | 0.1-0.2% |
| Laureth 3 | 0.1-2% |
| Lactic Acid | Q.S. to pH 5.5-6.0 |
| Deionized water | Balanced to 100% |

Example 13

An aftershave lotion may be prepared comprising the following ingredients:

| Ingredient | wt. % |
| --- | --- |
| Deionized water | 0.1-59.61% |
| Disodium EDTA | 0.1-0.02% |
| SD-Alcohol-40 | 0.1-15% |
| Phenoxyethanol (and) alkyl paraben | 0.1-0.6% |
| Sorbitol 70% | 0.1-3% |
| Citronellol polymer (emollient) | 0.1-13% |
| Bisabolol | 0.1-0.2% |

-continued

| Ingredient | wt. % |
| --- | --- |
| Tocopheryl Acetate | 0.1-0.8% |
| Coco-caprylate | 0.1-0.8% |
| Aluminum Starch Octenyl succinate | 0.1-5% |
| Polysorbate-85 | 0.1-1.5% |
| Fragrance | 0.1-1% |
| D & C Green No. 5 (0.1% solution)/Color | 0.1-0.07% |

Example 14

A clear shaving gel composition may be prepared comprising the following ingredients:

| Ingredient | wt. % |
| --- | --- |
| Deionized water | 0.1-46.5% |
| Glucamate DOE-120/PEG 120 Methyl Glucose Dioleate | 0.1-3% |
| Sodium Laureth Sulfate | 0.1-25% |
| Cocamidopropyl Hydroxy Sultaine | 0.1-20% |
| Phytoderm Complex G/ Propylene Glycol (and) Licorice Extract | 0.1-1% |
| Citronellol Polymer (surfactant) | 0.1-2.5% |
| Preservatives | Q.S. |
| Fragrance | Q.S. |

We claim:

1. A personal care composition comprising a compound according to Formula I below:

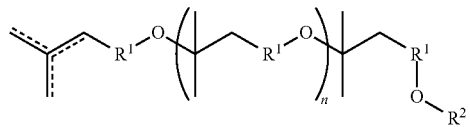

wherein $R^1$ is optionally substituted $C_1$-$C_{12}$ alkyl; $R^2$ is H, $C_{1-20}$alkyl, aryl, aryl-$C_{1-2}$ alkyl, optionally unsaturated alkyl esters or aryl esters, or $R^2$ is a moiety:

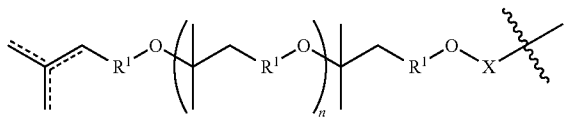

wherein X is a diacyl moiety of formula —C(O)—$R^3$—C(O)—, wherein $R^3$ is optionally substituted $C_{1-22}$ alkyl, optionally substituted $C_{2-22}$ alkenyl or optionally substituted aryl; and wherein n is an integer between 0 and 20;
wherein the composition is a toothpaste, mouthwash, mascara, lipstick, lip liner, or lip balm;
or wherein the composition is a hair shampoo which further comprises sodium laureth sulfate, cocamidopropyl betaine, coco-glucoside, ethylene glycol distearate, and laureth-3.

2. The personal care composition according to claim 1, wherein in the compound of Formula I, $R^1$ is optionally substituted linear $C_1$-$C_{12}$ alkyl or optionally substituted branched $C_1$-$C_{12}$ alkyl.

3. The personal care composition according to claim 1, wherein in the compound of Formula I, $R^1$ is unsubstituted branched $C_3$-$C_{12}$ alkyl.

4. The personal care composition according to claim 1, wherein in the compound of Formula I, $R^1$ is $CH_2CH_2CH(CH_3)CH_2CH_2$.

5. The personal care composition according to claim 1, wherein in the compound of Formula I, $R^2$ is H.

6. The personal care composition according to claim 1, wherein in the compound of Formula I, $R^2$ is $C_1$—$C_{12}$ alkyl.

7. The personal care composition according to claim 1, wherein in the compound of Formula I, $R^2$ is C(O)—$C_{1-6}$ alkyl and said $C_{1-6}$ alkyl is selected from methyl, ethyl, propyl, isopropyl, n-butyl, isobutyl, sec-butyl, tert-butyl, n-pentyl, or n-hexyl.

8. The personal care composition according to claim 1, wherein in the compound of Formula I, n is 0 to 10.

9. The personal care composition according to claim 1, wherein in the compound of Formula I, n is 0, 1, 2, 3, or 4.

10. The personal care composition according to claim 1, wherein in the compound of Formula I, $R^1$ is $CH_2CH_2CH(CH_3)CH_2CH_2$, n is 0-3 and $R^2$ is C(O)—$C_{1-20}$ alkyl, or C(O)—$C_{1-6}$ alkyl.

11. The personal care composition according to claim 1, wherein the composition comprises a single compound according to claim 1, the compound being present in an amount of 0.1 to 50% by weight of the composition.

12. The personal care composition according to claim 1, wherein the composition comprises one or more compounds, wherein each compound is independently a compound described in claim 1, each compound being present in an amount of 0.01 to 40% by weight of the composition.

13. The personal care composition according to claim 1, wherein the composition is a toothpaste, mouthwash, mascara, lipstick, lip liner, or lip balm; and wherein the composition further comprises at least one cosmetic active or cosmetically acceptable excipient selected from the group consisting of water, a diluent or carrier, a liquid polymer, a surfactant, a hydrotrope, an emollient, an emulsifier, a stabilizer, a preservative, a humectant, a rheological additive, an antioxidant, a fragrance, a fragrance carrier, a fragrance fixer, a texturizer, a color or pigment, and a thickener, optionally wherein any one or more cosmetic actives or excipients are organically sourced and/or renewable and/or vegan.

14. The personal care composition according to claim 13, wherein the one or more cosmetic actives or cosmetically acceptable excipients are selected from the group consisting of renewable plants or materials derived from renewable plants, soy oil, beeswax, rosemary oil, vitamin E, sunflower seed oil, jojoba butter, avocado oil, jojoba seed oil, grape seed oil, coconut oil, hydrogenated vegetable oil, peppermint oil, lavender oil, sandalwood oil, bergamot oil, rose oil, chamomile oil, ylang-ylang oil, tea-tree oil, jasmine oil, lemon oil, clementine oil, coriander seed oil, corn mint oil, eucalyptus lemon oil, geranium oil, ginger oil, key lime oil, basil oil, kukui nut seed oil, shea butter, hemp seed oil, hydrogenated grape seed oil, meadowfoam seed oil, mango seed butter, rice bran seed oil, rosehip fruit oil, soy lecithin, cupuacu seed butter, pumpkin seed oil, chamomile flower extract, bergamot fruit oil, palmarosa oil, lavender oil, rosemary extract, clary sage oil, cocoa butter, soybean oil, calendula flower extract, jasmine absolute, castor oil, pentaerythritol tetra-isostearate, candelilla wax, myristyl lactate, petrolatum, carnauba, ozokerite wax, cetyl esters, behenyl erucate, diisopropyl sebacate, propylene glycol stearate, corn starch, polyethylene glycol, polyethylene glycol laurate, myreth 3-laurate, acetamide monoethanolamine, isostearamidopropyl laurylacetodimonium chloride, ethylenediamine tetraacetic acid, disodium dimethicone copolyol sulfosuccinate, triethanolamine, boron nitride, hexamethyl disiloxane, trifluoropropyl polysiloxane, glyceryl stearate, PEG-100 stearate, benzophenone-3, mineral oil, caprylic/capric triglyceride, lauryl lactate, carbomer, diazolidinyl urea, coco-glucoside, ethylene glycol distearate, D-panthenol, methyldibromo glutaronitrile, laureth-3, lactic acid, SD-Alcohol 40, bisabolol, tocopherol acetate, coco-caprylate, PEG-120 methyl glucose dioleate, cocamidopropyl hydroxy sultaine, and licorice extract, optionally wherein any preceding ingredient is organically sourced.

15. The personal care composition according to claim 1, wherein the one or more Compounds of Formula I perform the function of a diluent or carrier, surfactant, emollient, stabilizer, preservative, humectant, rheological additive, antioxidant, fragrance, fragrance carrier, fragrance fixer, thickener, UV light absorber, and/or silicone or petroleum jelly replacement.

16. The personal care composition according to claim 1, wherein the composition comprises less than 10% by weight of any silicone polymer.

17. The personal care composition according to claim 1, wherein the composition is a mascara, lipstick, lip liner, or lip balm.

18. The personal care composition according to claim 13, wherein the composition further comprises at least one ingredient selected from aluminum zirconium tetrachlorohydrex gly, aluminum starch octenyl succinate, a poloxamer, a vegetable oil, a cyclomethicone, sodium lauryl sulfate, sodium laureth sulfate, polysorbate-80, polysorbate-20, polysorbate-85, cocamidopropyl betaine, polyquaternium-30), propylene glycol, glyceryl stearate, cetyl alcohol, stearic acid, phenoxyethanol, DMDM hydantoin, iodopropynyl butylcarbamate, alkyl paraben, glycerol, sorbitol, xylitol, isopropyl myristate, silica dimethyl sulfate, vitamin A or E, butylated hydroxytoluene, butylated hydroxyanisole, silica, titanium dioxide, iron oxide, mica, and triglycerides.

19. The personal care composition according to claim 1, wherein the compound of Formula I is selected from a structure:

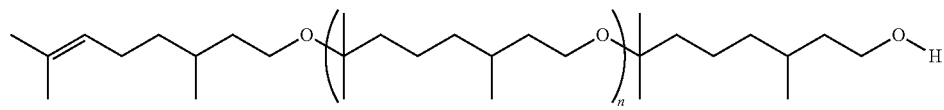

or

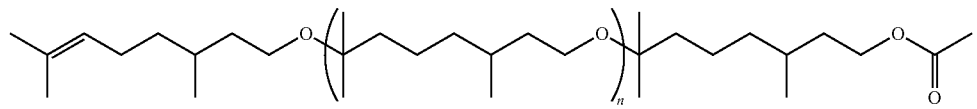

wherein in each of said compounds of Formula I, n is 0, 1, 2, 3, or 4.

20. A personal care composition according to claim 19, wherein the composition comprises a mixture of compounds of Formula I as set forth in claim 19, wherein said mixture of compounds vary only in the integer n, and wherein the mixture of compounds has (i) a average molecular weight ($M_n$), of 150 to 2000 Daltons, and (ii) a polydispersity ($M_w/M_n$) in the range of 1 to 5.

21. A personal care composition, wherein the composition is a lip balm, and wherein the composition comprises a compound of Formula I according to the structure:

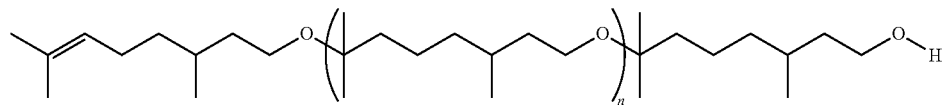

or

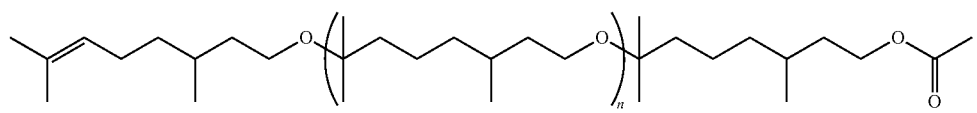

wherein in each of said compounds of Formula I, n is 0, 1, 2, 3, or 4;

wherein the composition further comprises water, one or more fragrances, and one or more glycol solutions.

22. The personal care composition according to claim 20, wherein the composition is a toothpaste, mouthwash, mascara, lipstick, lip liner, or lip balm.

* * * * *

UNITED STATES PATENT AND TRADEMARK OFFICE
CERTIFICATE OF CORRECTION

PATENT NO. : 11,872,300 B2  
APPLICATION NO. : 17/185619  
DATED : January 16, 2024  
INVENTOR(S) : Patrick Foley and Ashoke Bhattacharjee Page 1 of 1

It is certified that error appears in the above-identified patent and that said Letters Patent is hereby corrected as shown below:

In the Specification

Column 4, Line 25, "C(O)—$C_{1\_20}$ alkyl" should be changed to "C(O)—$C_{1-20}$ alkyl"

Column 5, Line 19-20, "C(O)—$C_1$-20 alkyl" should be changed to "C(O)—$C_{1-20}$ alkyl"

Column 5, Line 34, "C(O)—$C_{7\_20}$ alkyl" should be changed to "C(O)—$C_{7-20}$ alkyl"

Column 17, Line 36, "$C_5$-Cao arylsulfinyl" should be changed to "$C_{5-20}$ arylsulfinyl"

Signed and Sealed this  
Twenty-seventh Day of August, 2024

Katherine Kelly Vidal  
*Director of the United States Patent and Trademark Office*